US006679892B2

(12) United States Patent
Guido et al.

(10) Patent No.: US 6,679,892 B2
(45) Date of Patent: Jan. 20, 2004

(54) SURGICAL DEVICE FOR LIGATING AND SEVERING VESSELS

(75) Inventors: Ron Guido, Annandale, NJ (US); Robert Nering, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 67 days.

(21) Appl. No.: 09/966,792

(22) Filed: Sep. 28, 2001

(65) Prior Publication Data

US 2003/0065335 A1 Apr. 3, 2003

(51) Int. Cl.[7] ............................................. A61B 17/12
(52) U.S. Cl. ..................... 606/113; 606/139; 606/144
(58) Field of Search .............................. 606/113, 139, 606/144, 148; 289/17

(56) References Cited

U.S. PATENT DOCUMENTS 3,476,115 A * 11/1969 Graeff et al. ............... 606/139
5,290,284 A * 3/1994 Adair ........................... 606/37
5,330,491 A * 7/1994 Walker et al. .............. 606/148
5,486,186 A * 1/1996 Yoon ........................... 606/148
5,814,052 A * 9/1998 Nakao et al. ............... 606/115

* cited by examiner

Primary Examiner—Julian W. Woo

(57) ABSTRACT

A surgical device for ligating and severing a vessel. The surgical device including: a housing; a flexible suture having a looped portion extending from a distal end of the housing for capturing a periphery of the vessel; ligating means for tightening the looped portion around the periphery of the vessel; and a cutter for cutting the vessel. Also provided is a method for ligating and severing a vessel including: looping a flexible suture material around a periphery of the vessel; looping a flexible cutting material around the periphery of the vessel; ligating the vessel by decreasing the size of the loop of flexible suture material; and severing the vessel by decreasing the size of the loop of flexible cutting material. The method preferably further includes drawing the vessel against a cutting surface, such as a knife blade, which is retractable in a housing.

19 Claims, 5 Drawing Sheets

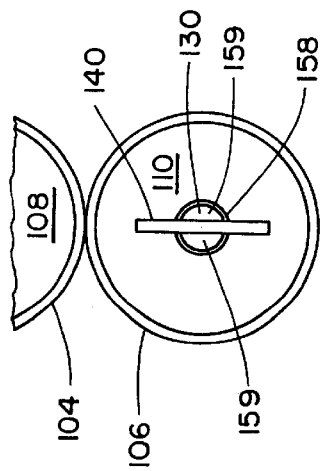
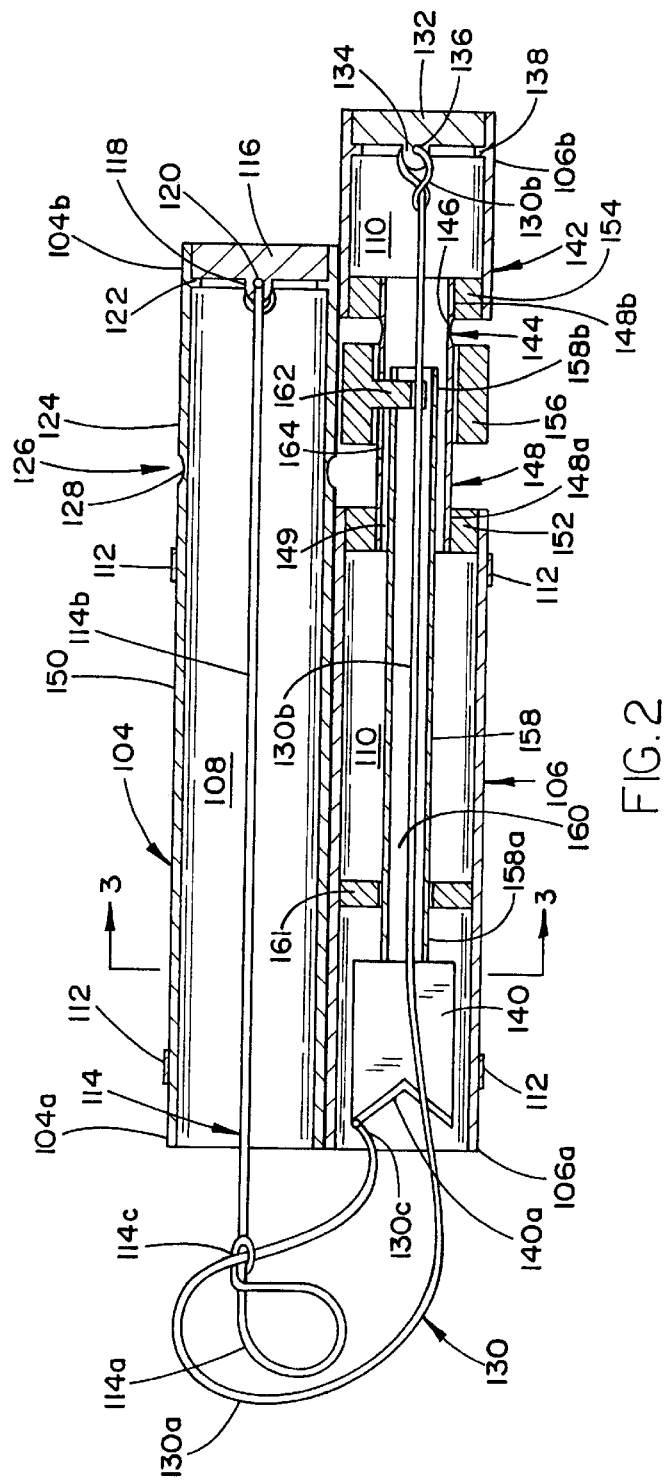

SURGICAL DEVICE FOR LIGATING AND SEVERING VESSELS

BACKGROUND OF THE INVENTION

1. Field of the Invention

The present invention relates generally to surgical devices, and more particularly, to a surgical device for ligating, and severing vessels.

2. Prior Art

Methods for ligating and transecting vessels via endoscopic means are known in the art. One method involves use of scissors and ligating clips. Two tools are required for this approach, thus complicating the procedure by excess tool exchanges. Furthermore, the placed clips can hinder subsequent movement of instruments. Finally, foreign bodies (clips) are left in the patient's body.

Another approach involves the use of a knife placed between two wire guides that are capable of applying a current across a vessel. This design can potentially result in the spread of thermal energy to unintended portions of the vessel to be transected, potentially compromising its utility. Still yet another approach involves the use of scissor-like clamping jaws that open around a vessel, and then must be closed, whereby a current is applied to the vessel from within the jaws. However, these types of instruments are difficult to use in confined spaces because of the upward opening movement of at least one of the jaws often causes an interference with objects in the field. Further, the upward opening jaw obscures the vision of the surgeon using the device, particularly in endoscopic procedures.

Both saphenous veins and radial arteries are used as conduits in coronary artery bypass surgery. Conventional techniques for harvesting these vessels involve an incision length approximately equal to the length of the vessel being harvested. Recently, various bipolar endoscopic vessel-harvesting devices have been developed as a means of removing saphenous veins or radial arteries in a minimally invasive manner.

Users of these devices frequently struggle to separate side branches of the veins or arteries when said side branches run beneath or above the main trunk of the vessel. In addition, the visualization of the vessel may be lost in excess adipose tissue. Finally, the user friendliness of these devices is subject to question since the steps involved in identifying, securing, and dissection/ligation of side branches is not always intuitive, i.e., the user frequently has to concentrate on what his or her hands are doing and not the vessel at hand. Current bipolar devices also fail to complete the terminal ligation required to excise the vein or artery.

SUMMARY OF THE INVENTION

Therefore it is an object of the present invention to provide a surgical device for ligating and severing a vessel, which is friendlier to use than the devices of the prior art.

It is another object of the present invention to provide a surgical device for ligating and severing a vessel, which eliminates the need for ligating clips to ligate the vessel.

It is yet another object of the present invention to provide a surgical device for ligating and severing a vessel, which eliminates the use of thermal energy so as not to compromise the utility of the vessel.

It is yet another object of the present invention to provide a surgical device for ligating and severing a vessel, which eliminates the necessity of opening and closing scissor-like jaws.

It is still yet another object of the present invention to provide a surgical device for ligating and severing a vessel, which minimizes the need for multiple instrument exchanges.

Accordingly, a surgical device for ligating and severing a vessel is provided. The surgical device comprising: a housing; a flexible suture having a looped portion extending from a distal end of the housing for capturing a periphery of the vessel; ligating means for tightening the looped portion around the periphery of the vessel; and cutting means for cutting the vessel.

Preferably, the flexible suture further comprises an extended portion disposed in the housing and proximal to the looped portion. The housing preferably comprises at least a first tube, the extended portion of the suture being disposed in the first tube, the looped portion being extended from a distal end of the first tube. Preferably a transition between the looped and extended portions of the flexible suture comprises a slipknot.

The ligating means preferably comprises a first handle disposed on the first tube, the first handle being connected to a proximal end of the extended portion of the flexible suture such that a proximal movement of the first handle extends the extended portion of the flexible suture and decreases a loop size of the looped portion of the flexible suture to ligate the vessel captured therein. Preferably, the first handle is connected to a proximal end of the first tube by a breakaway joint.

The cutting means preferably comprises: a flexible cutting material having a looped portion extending from the distal end of the housing for capturing a periphery of the vessel, the flexible cutting material further having an extended portion; and cutting material actuation means disposed in the housing for tightening the looped portion of the flexible cutting material around the periphery of the vessel and for drawing the vessel against a cutting surface. The housing preferably comprises at least a second tube, the extended portion of the flexible cutting material being disposed in the second tube, the looped portion being extended from a distal end of the second tube.

The cutting material actuation means preferably comprises a second handle disposed on the second tube, the second handle being connected to a proximal end of the extended portion of the cutting material such that a proximal movement of the second handle decreases a loop size of the looped portion of the flexible cutting material and draws the vessel against the cutting surface to sever the vessel captured therein. The second handle is preferably connected to a proximal end of the second tube by a breakaway joint.

Preferably, the cutting surface is a cutting edge of a knife blade, the knife blade being disposed in the distal end of the second tube. The knife blade is preferably movably disposed in the second tube and further comprising knife blade actuation means for moving the knife blade in the second tube between an extended position and a retracted position, in which case, the knife cooperates with the cutting material to sever the vessel when in the extended position. The knife blade actuation means preferably comprises a third handle slidingly disposed on the second tube and operatively connected to the cutting blade by a control rod disposed in an internal lumen of the second tube, wherein movement of the third handle in the distal direction moves the knife blade into the extended position and movement of the third handle in the proximal direction moves the knife blade into the retracted position.

Also provided is a method for ligating and severing a vessel. The method comprising: looping a flexible suture material around a periphery of the vessel; looping a flexible cutting material around the periphery of the vessel; ligating the vessel by decreasing the size of the loop of flexible suture material; and severing the vessel by decreasing the size of the loop of flexible cutting material.

Preferably, the method further comprises drawing the vessel against a cutting surface. Preferably, the cutting surface is a knife blade, in which case the method further comprises extending the knife blade distally to interact with the flexible cutting material and vessel.

Preferably, the flexible suture material comprises a looped portion, an extended portion extending from the looped portion, and a slipknot at the transition between the looped and extended portions, in which case the severing step further comprises severing the extended portion of the flexible suture material.

BRIEF DESCRIPTION OF THE DRAWINGS

These and other features, aspects, and advantages of the apparatus and methods of the present invention will become better understood with regard to the following description, appended claims, and accompanying drawings where:

FIG. 2 illustrates a sectional view of the surgical device of FIG. 1 taken along line 2—2.

FIG. 3 illustrates a sectional view taken along line 3—3 of FIG. 2.

DETAILED DESCRIPTION OF THE PREFERRED EMBODIMENT

The surgical device of the present invention is preferably configured as a disposable device, however, the surgical device can also be configured as semi-reusable or reusable without departing from the scope or spirit of the present invention.

Figure 1:
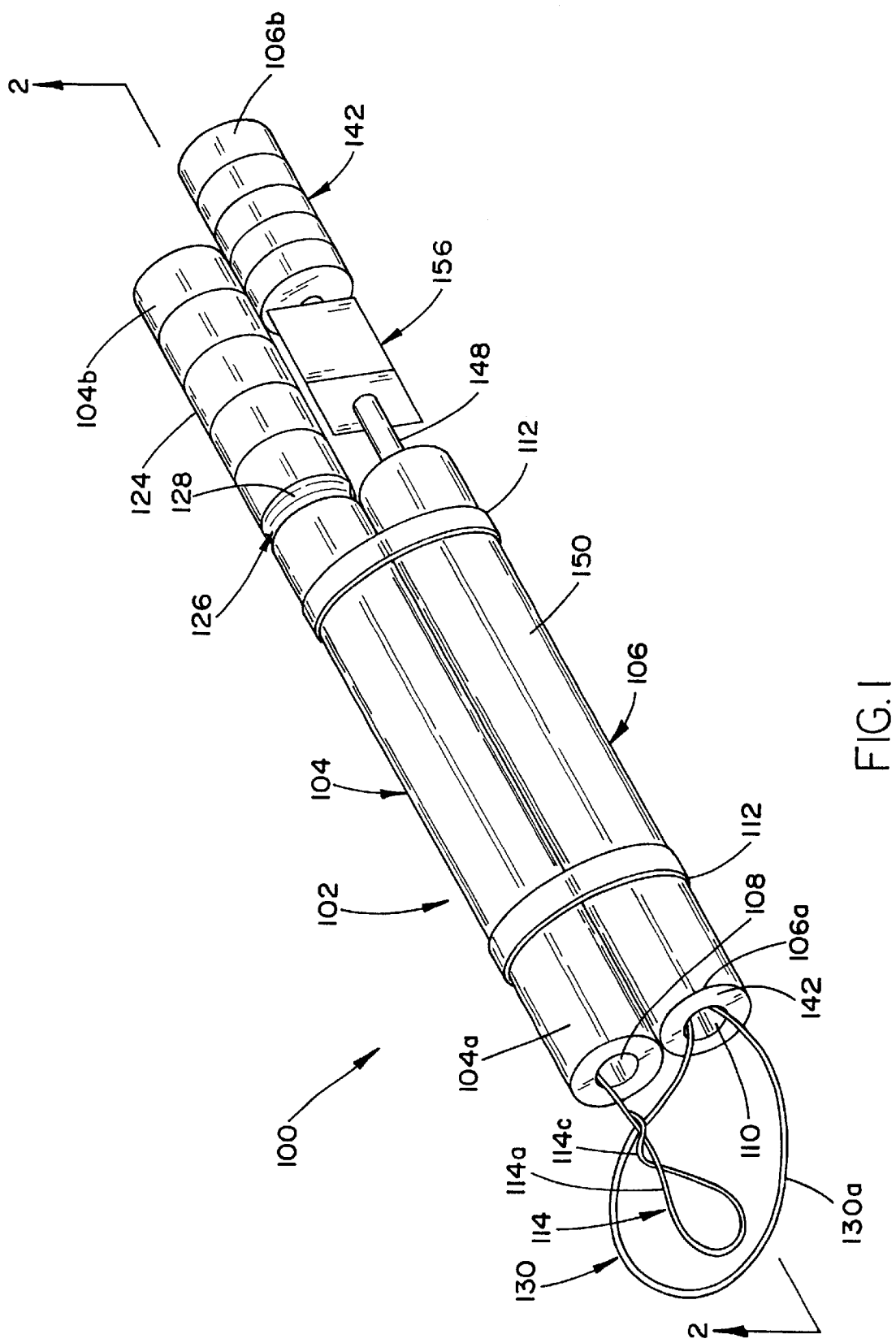
FIG. 1 illustrates an isometric view of a preferred implementation of the surgical device of the present invention.

Referring now to FIGS. 1–3, a surgical device for ligating and severing a vessel is illustrated therein, and being generally referred to by reference numeral 100. The surgical device includes a housing 102. Preferably, the housing comprises first and second tubes 104, 106. Each of the first and second tubes 104, 106 preferably has an internal lumen 108, 110. The first and second tubes 104, 106 are preferably separate tubes fabricated from a resilient medical grade material, such as a thermoplastic or stainless steel and connected together by any means known in the art, such as by one or more bands 112, welding, adhering, etc.

In an endoscopic configuration, the first and second tubes 104, 106 should be of sufficient length for the particular endoscopic procedure envisioned. Although, the surgical device of the present invention has particular utility as an endoscopic instrument, its use is not limited to such. The surgical devices 100 of the present invention can also be used and configured for open surgical procedures. Furthermore, the first and second tubes are shown and described as separate tubes that are connected together, however, those skilled in the art will realize that they can be integrally formed without departing from the scope or spirit of the present invention.

A flexible suture material 114 is disposed in the lumen 108 of the first tube 104. The suture material 114 has a looped portion 114a extending from a distal end 104a of the housing 102, and in particular, from the first tube 104. As will be described below, the looped portion 114a is used to capture a periphery of a vessel to be ligated and transected. The flexible suture further has an extended portion 114b disposed in the lumen 108 of the first tube 104 and proximal to the looped portion 114a. A proximal end of the extended portion 114b is preferably anchored to the first tube 102.

Preferably, a first plug 116 is provided in the proximal end 104b of the first tube 104 and having a projection 118 and hole 120 for anchoring the extended portion 114b of the suture 114 thereto. Alternatively, the first plug 116 can simply have a hole therein (not shown) through which the suture material 114 is passed. In which case, a knot (not shown) can be provided which is larger than the diameter of the hole such that the suture cannot be pulled distally. The first plug 116 is preferably fabricated from the same material as the first tube and is press fit or epoxied in place. A shoulder 122 can also be provided in the interior of the lumen 108 for preventing further axial movement of the first plug 116 in the distal direction.

Preferably, a transition between the looped and extended portions 114a, 114b of the flexible suture 114 is a slipknot 114c. The slipknot 114c, as will be discussed below, allows the diameter of the looped portion 114a to be decreased when the extended portion 114b is pulled proximally. Tying slip knots is well known in the art. Flexible suture materials for ligating vessels are also well known in the art, such as Prolene manufactured by.

The surgical device 100 also includes ligating means for tightening the looped portion 114a around the periphery of the vessel. The ligating means preferably comprises a first handle 124 disposed on the proximal end 104b of the first tube 104. The first handle 124 is preferably connected at the proximal end 104b of the first tube 104 by a breakaway joint 126. Breakaway joints 126 are well known in the art, such as by providing a reduced cross-sectional thickness, which facilitates breaking of the first handle 124 from the first tube 104. The reduced thickness is preferably accomplished by providing a groove 128 in an exterior wall of the first tube 104.

Since the first handle 124 is connected to a proximal end of the extended portion 114b of the flexible suture 114, after breaking away from the first tube 104, a proximal movement of the first handle 124 extends the extended portion 114b of the flexible suture 114 through the slipknot 114c and decreases the loop diameter of the looped portion 114a of the flexible suture 114 to ligate a vessel captured therein.

Also provided in the surgical device 100 of the present invention is cutting means for cutting the vessel captured by the looped portion 114a of the suture material 114. The cutting means preferably comprises a flexible cutting material 130 having a looped portion 130a extending from a distal end 106a of the second tube 106 for capturing a periphery of the vessel. The flexible cutting material 130 also preferably has an extended portion 130b disposed in the lumen 110 of the second tube 106. The flexible cutting material 130 is preferably fixed at a distal end 130c near the distal end 106a of the second tube 106 and is also fixed at a proximal end 130d near a proximal end 106b of the second tube 106. The flexible cutting material 130 is preferably fabricated from a resilient medical grade material such as stainless steel wire having a small diameter useful for slicing through tissue.

Preferably, a second plug 132 is provided in the proximal end 106b of the second tube 106 and having a projection 134 and hole 136 for securing the extended portion 130b of the cutting material 130 thereto. Alternatively, the second plug 132 can simply have a hole therein (not shown) through which the cutting material 130 is passed. In which case, a knot (not shown) can be provided which is larger than the diameter of the hole such that the cutting material cannot be pulled distally. The second plug 132 is preferably fabricated from the same material as the second tube 106 and is press fit or epoxied in place. A shoulder 138 can also be provided in the interior of the lumen 110 for preventing further axial movement of the second plug 132 in the distal direction.

The distal end 130c of the cutting material 130, as will be discussed below, is preferably fixed to a cutting surface, such as a knife blade 140 slidingly disposed in the lumen 110 of the second tube 106. Alternatively, the distal end 130c of the cutting material 130 can be fixed to the distal end 106a of the second tube 106 by any means known in the art.

The surgical device 100 also preferably has a cutting material actuation means preferably disposed in the second tube 106 for tightening the looped portion 130a of the flexible cutting material 130 around the periphery of the vessel and for drawing the vessel against a cutting surface 140a. Although the cutting surface 140a can simply be an end surface 142 of the second tube 106, it is preferred that the cutting surface 142 be a cutting edge 140a of the slidable knife blade 140. As will be discussed below, the cutting material 130 does not have to actually cut the vessel. Where the cutting surface is itself able to cut the vessel, such as the cutting edge 140a, the cutting material 130 merely draws the vessel against the cutting edge 140a and it is the cutting edge 140a, which severs the vessel.

The cutting material actuation means preferably comprises a second handle 142 disposed at the proximal end 106b of the second tube 106. The second handle 142 is preferably connected at the proximal end 106b of the second tube 106 by a breakaway joint 144. As discussed above, such breakaway joints 126 are well known in the art, such as by providing a reduced cross-sectional thickness, which facilitates breaking of the second handle 142 from the second tube 106. The reduced thickness is preferably accomplished by providing a groove 146 in a third tube 148, which for purposes of this disclosure, is considered part of the second tube 106.

Since the second handle 142 is connected to a proximal end of the extended portion 130b of the flexible cutting material 130, after breaking away from the second tube 106, a proximal movement of the second handle 142 decreases a loop size of the looped portion 130a of the flexible cutting material 130 and draws the vessel against the cutting surface 140a to sever the vessel captured therein.

To facilitate the transection of the vessel, a knife blade 140 provides the cutting surface 140a. The knife blade 140 is preferably slidingly disposed in the lumen 110 in the distal end 106a of the second tube 106. The knife blade 140 is preferably fabricated from a resilient medical grade hardened material such as hardenable stainless steel where at least the cutting edge 140a is hardened to maintain a sharp cutting edge throughout the expected life of the surgical device 100. As discussed above, the distal end 130c of the cutting material 130 is preferably connected, such as by soldering, to the cutting edge 140a of the knife blade 140 to ensure that the vessel is drawn to the cutting edge 140a when the second handle 142 is broken away and pulled proximally.

Also provide is a knife blade actuation means for moving the knife blade 140 in the lumen 110 of the second tube 140 between an extended position (shown in FIG. 6) and a retracted position (shown in FIG. 2), wherein the knife blade 140 cooperates with the cutting material 130 to sever the vessel when in the extended position. The knife blade actuation means preferably comprises the third tube 148 disposed between a first portion 150 of the second tube 106 and a second portion of the second tube 106, where the second portion preferably comprises the second handle 142. Distal and proximal ends 148a, 148b of the third tube 148 are preferably affixed to the first portion 150 and second handle 142 by press fit, weld, or epoxy into corresponding plugs 152, 154 which themselves are preferably, press fit, welded or epoxied into the lumen 110 of the second tube 106.

A third handle 156 is slidingly disposed on the third tube 150 and operatively connected to the knife blade 140. The knife blade 140 is preferably connected to the third handle 156 by a control rod 158 disposed in the lumen 110 of the second tube 106. The control rod 158 preferably has a lumen 160 and is fixed or integrally formed at a distal end 158a to the knife blade 140. A proximal end 158b of the control rod 158 is preferably disposed in a lumen 149 of the third tube 148 and is fixed to the third handle 156 at a proximal end 158b.

The third handle 156 preferably has a projection 162, which rides in a corresponding slot 164 in the third tube 148. The projection 162 is preferably fixed to a corresponding hole (not shown) in the control rod 158. With such an arrangement, those skilled in the art will appreciate that a movement of the third handle 156 in the distal direction results in a corresponding distal movement of the knife blade 140 into the extended position and movement of the third handle 156 in the proximal direction results in a corresponding distal movement of the knife blade 140 into the retracted position. As shown in FIG. 3, the extended portion 130b of the cutting material 130 is preferably threaded through the lumen 149 of the third tube 148 and the lumen 160 of the control rod 158 to exit the distal end 158a of the control rod 158 through a distal opening 159. A guide 161 can be provided to maintain a central axial position of the control rod 158 in the lumen 110 and to prevent the knife blade 140 from interfering with the internal walls of the lumen 110 of the second tube 106.

Figure 4:
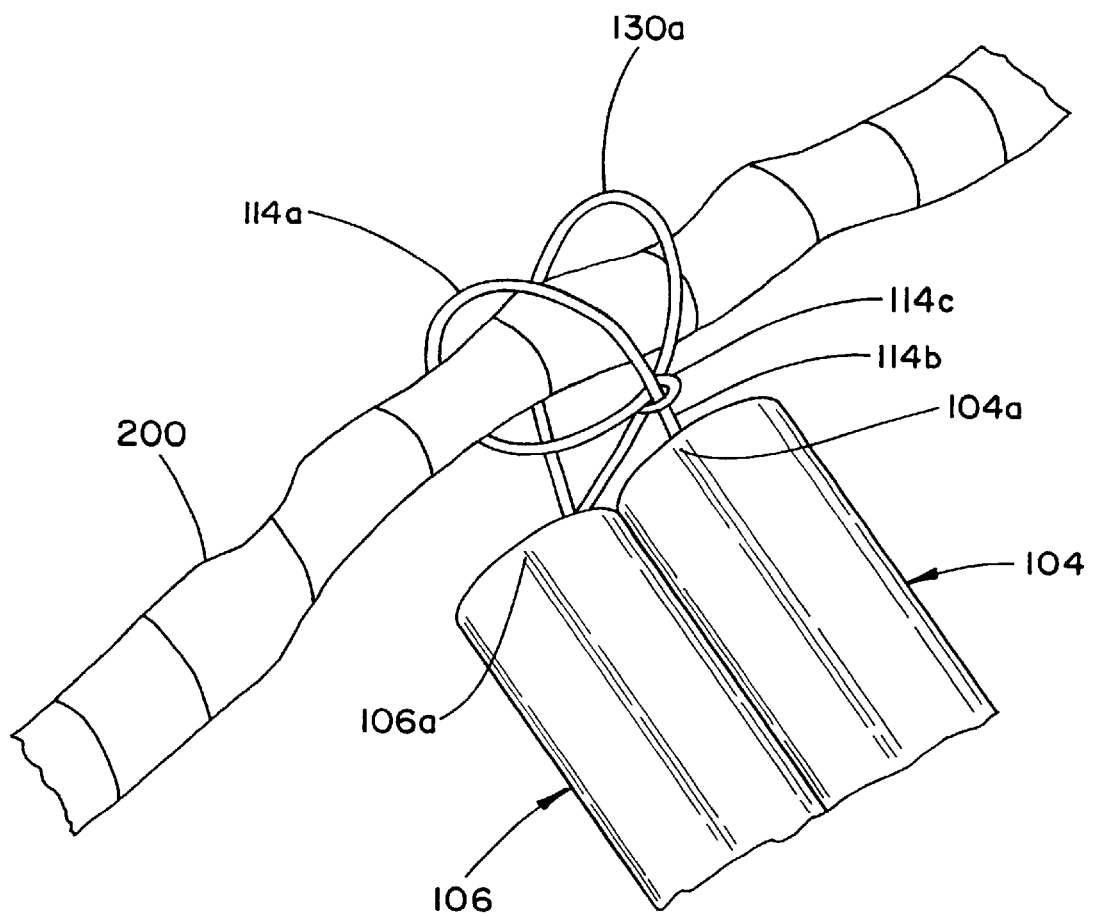
FIG. 4 illustrates an isometric view of the distal end of the surgical device of FIG. 1 wherein a vessel is ensnared by the suture and cutting material.

The operation of the surgical device 100 will now be described with regard to FIGS. 4–6. Referring first to FIG. 4, there is shown both the looped portion 114a of the suture material 114 and the looped portion 130a of the cutting material 130a looped around a vessel 200 to be ligated and transected. As shown in FIG. 4, the looped portions 114a, 130a of the suture and cutting materials 114, 130 ensnare a periphery of the vessel 200. Preferably, one leg of the looped portion 130a of the cutting material 130 is threaded through a portion of the slipknot 114c. As will be described later, this facilitates cutting the extending portion 114b of the suture when the vessel 200 is transected. However, the looped portion 130a of the cutting material 130 can be offset a predetermined distance from the suture material 114 and the extended portion 114b of the suture material can be cut in another way, such as by using another instrument.

Figure 5:
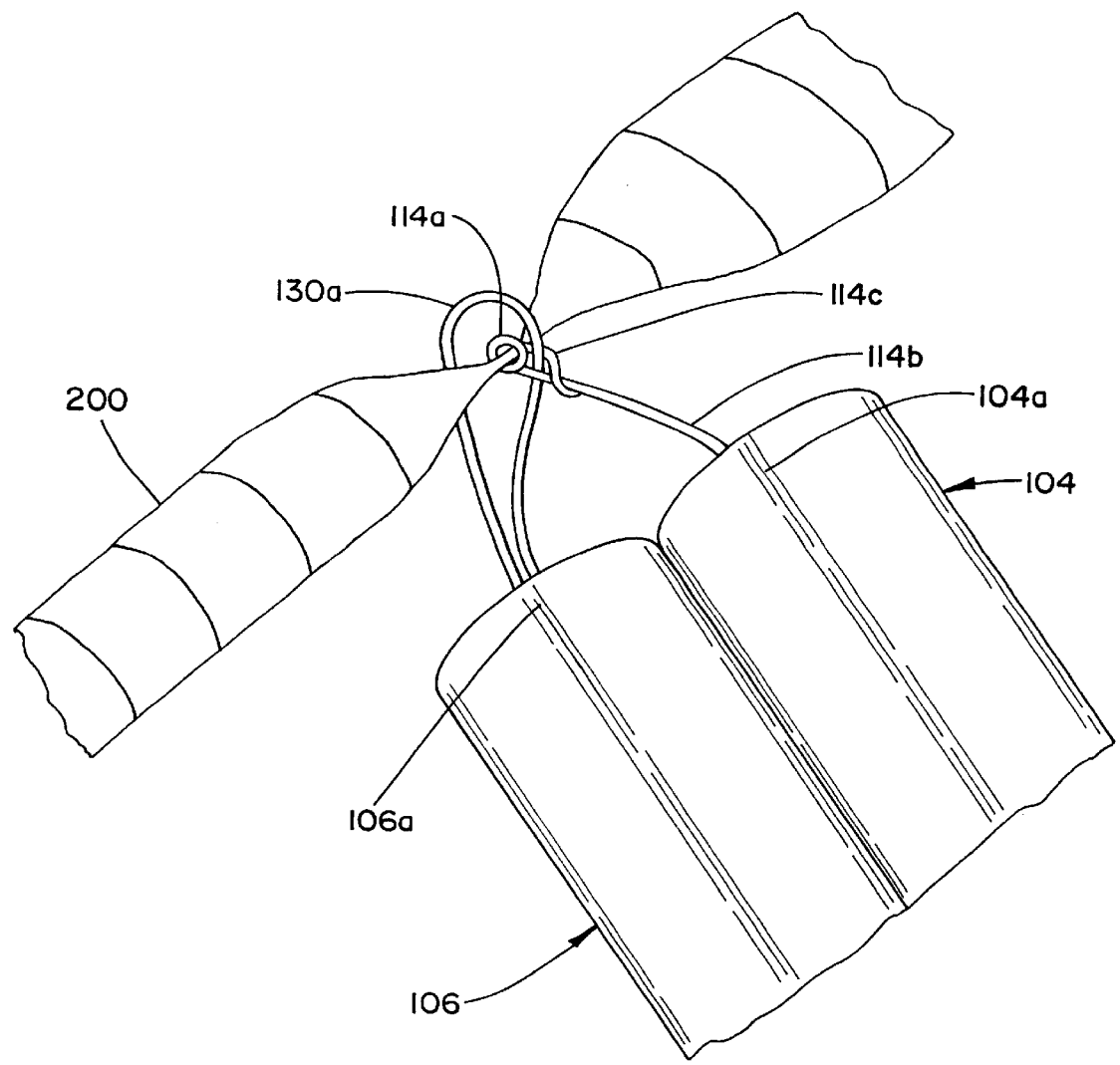
FIG. 5 illustrates an isometric view of the surgical device of FIG. 4 wherein the vessel is ligated with the suture material.

Referring now to FIG. 5, the first handle 124 is broken away from the first tube 104 about the breakaway joint 126 and pulled proximally relative to the distal end 104a of the first tube 104. The proximal movement of the first handle 124 extends the extended portion 114b of the suture material 114 through the slipknot 114c, which results in a decrease in the size of the looped portion 114a. The looped portion 114a of the suture material 114 therefore ligates the vessel 200.

Figure 6:
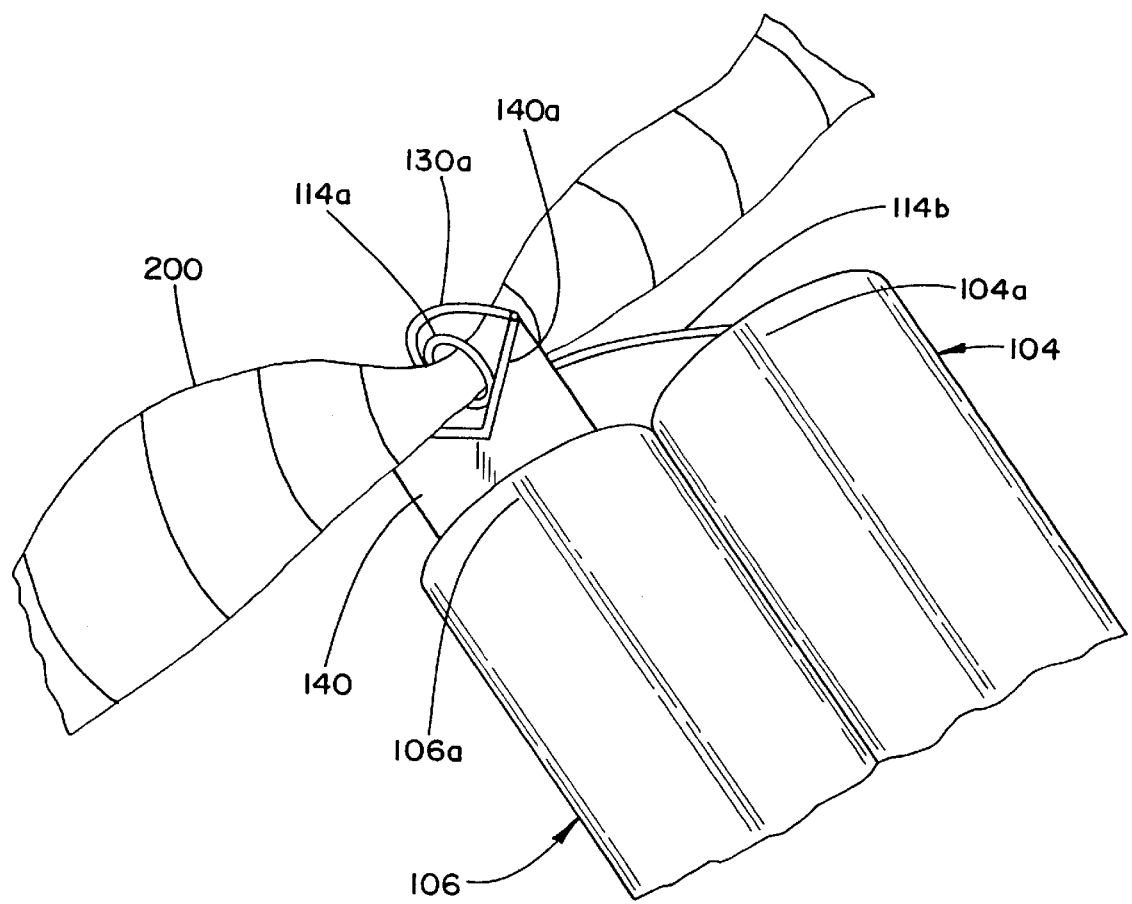
FIG. 6 illustrates an isometric view of the surgical device of FIG. 5 wherein the vessel is about to be transected by the cutting material and knife blade.

Referring now to FIG. 6, the vessel is severed or transected by breaking away the second handle 142 about breakaway joint 144 and pulling the second handle 142 proximally relative to the distal end of the second tube 106. This results in decreasing the size of the looped portion 130a of flexible cutting material 130. The second handle 142 is continued to be pulled until the vessel 200 is brought into contact with the cutting surface and the cutting material 130 ultimately slices through the vessel 200. As discussed above, the cutting material 130 is threaded through the slipknot 114c in such a way so as to also sever the suture material 114 without releasing the ligation of the vessel 200.

Preferably, prior to breaking away the second handle 142, the knife blade 140 is extended to the extended position as shown in FIG. 6 by sliding the third handle 156 distally. After the knife blade 140 is extended, the second handle 142 is broken away and pulled proximally to force the vessel to bear against the cutting edge 140a of the knife blade 140 to facilitate the transection of the vessel 200 and the cutting of the suture 114. In this situation, it is not necessary for the cutting material 130 to cut through the vessel 200, but merely to gather the vessel 200 and draw it against the cutting surface 140a, which actually performs the cutting of the vessel 200.

Although, the device 100 is particularly useful for severing side branches of a vessel to be harvested in a coronary artery bypass graft procedure, it can also be utilized in other procedures such as ligation of fallopian tubes for fertility control, ligation and transection of bile ducts for nephrectomy, or for the transection of ligaments or other tissue structures.

EXAMPLE

As discussed above, the present invention has particular utility in a coronary artery bypass graft procedure (CABG), however, the use of the instruments of the present invention is now described with regard to the CABG procedure by way of example only and not to limit the scope or spirit of the present invention. A patient is prepared for cardiac surgery in a conventional manner using conventional techniques and procedures. The patient is then anesthetized and ventilated using conventional techniques. A conventional CABG procedure is performed by harvesting the greater saphenous vein from one or both of the patient's legs. The surgeon prepares an opening to the heart by dividing the patient's sternum (conventional median sternotomy) and spreading the rib cage apart using a surgical retractor. The surgeon next begins dissecting the internal mammary artery (IMA) from the chest wall of the patient, so that the distal end of the vessel may be anastomosed to the diseased lower anterior descending (LAD) coronary artery on the distal side of a lesion on the septum near the left ventricle of the heart as a source of oxygenated blood. During the surgical procedure, the surgeon optionally elects to have the patient's heart beating to perform a conventional beating heart CABG, although the surgeon has a cardiopulmonary bypass machine (CPB) primed with the patient's blood and available if it is necessary to convert the beating heart procedure into a conventional stopped heart procedure.

The surgeon prepares the heart for attaching the graft vessels by cutting and pulling away the pericardium. After checking the graft vessels for patency, collateral damage and viability, the surgeon prepares to do the anastomoses necessary to bypass the lesions in the coronary arteries. The surgeon sutures the proximal end of each graft vessel to the patient's aorta and the distal end to the diseased coronary artery, distal to the blockage or lesion. The distal end of the LAD is similarly anatomosed to a coronary artery distal to a lesion in a conventional manner. The surgeon checks the bypass grafts for adequate blood flow in a conventional manner, and then completes the remainder of the operation in a conventional manner.

The veins used in the CABG procedure are harvested endoscopically. Initially the patient's leg is positioned to be slightly bent and is turned to expose the inner leg. A marker is used to show on the skin the location of the vein to be harvested. Then an incision is created on the inner leg near the knee, through the skin and subcutaneous layers. The vein typically lies directly beneath the subcutaneous layers and so a middle portion of the vein is accessed through the incision. After some initial dissection with conventional blunt dissectors around this portion of the vein, a surgical instrument is introduced into the incision. An endoscope provides visualization of the vein and surrounding tissue within the working space inside the head. The instrument is advanced along the vein. Side branches off of the vein are ligated and divided a few millimeters away from the vein using the surgical device of the present invention, taking great care not to injure the vein in any way. The harvesting procedure continues in this manner until the vein is hemostatically isolated from surrounding tissues and blood supply along the portion to be harvested. Then stab incisions are created through the skin and subcutaneous layers at the distal and proximal ends of the vein, and the vessel is transected in order to remove the vein from the knee incision. Thee harvested vein is prepared for use as grafts in a conventional manner.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A surgical device for ligating and severing a vessel, the surgical device comprising:
   a housing;
   a flexible suture having a first looped portion extending from a distal end of the housing for capturing a periphery of the vessel;
   flexible cutting material having a second looped portion extending from the distal end of the housing, the second looped portion being threaded through the first looped portion and also for capturing the periphery of the vessel;
   ligating means for tightening the first looped portion around the periphery of the vessel; and
   cutting means for drawing the second looped portion and captured vessel against a cutting surface to sever the vessel.

2. The surgical device of claim 1, wherein the flexible suture further comprises an extended portion disposed in the housing and proximal to the first looped portion.

3. The surgical device of claim 2, wherein the housing comprises at least a first tube, the extended portion of the suture being disposed in the first tube, the first looped portion being extended from a distal end of the first tube.

4. The surgical device of claim 3, wherein a transition between the first looped and extended portions of the flexible suture comprises a slipknot.

5. The surgical device of claim 4, wherein the ligating means comprises a first handle disposed on the first tube, the first handle being connected to a proximal end of the extended portion of the flexible suture such that a proximal movement of the first handle extends the extended portion of the flexible suture and decreases a loop size of the first looped portion of the flexible suture to ligate the vessel captured therein.

6. The surgical device of claim 5, wherein the first handle is connected to a proximal end of the first tube by a breakaway joint.

7. The surgical device of claim 1, wherein the cutting means comprises:
cutting material actuation means disposed in the housing for tightening the second looped portion of the flexible cutting material around the periphery of the vessel and for drawing the vessel against the cutting surface.

8. The surgical device of claim 7, wherein the housing comprises at least a second tube, an extend portion of the flexible cutting material being disposed in the second tube, the second looped portion being extended from a distal end of the second tube.

9. The surgical device of claim 8, wherein the cutting material actuation means comprises a second handle disposed on the second tube, the second handle being connected to a proximal end of the extended portion of the cutting material such that a proximal movement of the second handle decreases a loop size of the second looped portion of the flexible cutting material and draws the vessel against the cutting surface to sever the vessel captured therein.

10. The surgical device of claim 9, wherein the second handle is connected to a proximal end of the second tube by a breakaway joint.

11. The surgical device of claim 8, wherein the cutting surface is a cutting edge of a knife blade, the knife blade being disposed in the distal end of the second tube.

12. The surgical device of claim 11, wherein the knife blade is movably disposed in the second tube and further comprising knife blade actuation means for moving the knife blade in the second tube between an extended position and a retracted position, wherein the knife cooperates with the cutting material to sever the vessel when in the extended position.

13. The surgical device of claim 12, wherein the knife blade actuation means comprises a third handle slidingly disposed on the second tube and operatively connected to the knife blade by a control rod disposed in an internal lumen of the second tube, wherein movement of the third handle in the distal direction moves the knife blade into the extended position and movement of the third handle in the proximal direction moves the knife blade into the retracted position.

14. A method for ligating and severing a vessel, the method comprising:
looping a flexible suture material around a periphery of the vessel;
looping a flexible cutting material around the periphery of the vessel and threading the flexible cutting material through a looped portion of the flexible suture material;
ligating the vessel by decreasing the size of the loop of flexible suture material; and
drawing the vessel against a cutting surface by decreasing the size of the loop of flexible cutting material to sever the vessel.

15. The method of claim 14, wherein the cutting surface is a knife blade and further comprising extending the knife blade distally to interact with the flexible cutting material and vessel.

16. The method of claim 14, wherein the flexible suture material comprises an extend portion extending from the looped portion, and a slip knot at the transition between the looped and extended portions, wherein the drawing step further comprises severing the extended portion of the flexible suture material.

17. A surgical device for ligating and severing a vessel, the surgical device comprising:
a housing;
a flexible suture having a loop portion extending from a distal end of the housing for capturing a periphery of the vessel;
ligating means for tightening the looped portion around the periphery of the vessel; and
cutting means for cutting the vessel, wherein the cutting means comprises a flexible cutting material having a looped portion extending from the distal end of the housing for capturing a periphery of the vessel, the flexible cutting material further having an extended portion and cutting material actuation means disposed in the housing for tightening the looped portion of the flexible cutting material around the periphery of the vessel and for drawing the vessel against a cutting surface,
wherein the housing comprises at least a tube, the extended portion of the flexible cutting material being disposed in the tube, the looped portion being extended from a distal end of the tube, the cutting surface being a cutting edge of a knife blade, the knife blade being disposed in the distal end of the tube, the knife blade being movably disposed in the tube and further comprising knife blade actuation means for moving the knife blade in the tube between an extended position and a retracted position, wherein the knife cooperates with the cutting material to sever the vessel when in the extended position, the knife blade actuation means comprising a handle slidingly disposed on the tube and operatively connected to the knife blade by a control rod disposed in an internal lumen of the tube, wherein movement of the handle in the distal direction moves the knife blade into the extended position and movement of the handle in the proximal direction moves the knife blade into the retracted position.

18. A method for ligating and severing a vessel, the method comprising:
looping a flexible suture material around a periphery of the vessel;
looping a flexible cutting material around the periphery of the vessel;
ligating the vessel by decreasing the size of the loop of flexible suture material;
drawing the vessel against a cutting surface, wherein the cutting surface is a knife blade:,
extending the knife blade distally to interact with the flexible cutting material and vessel; and
severing the vessel by decreasing the size of the loop of flexible cutting material.

19. A surgical device for ligating and severing a vessel, the surgical device comprising:
a flexible suture having a looped portion extending from a distal end of the housing for capturing a periphery of the vessel, the flexible suture having an extended portion extending from the looped portion;
ligating means for tightening the looped portion around the periphery of the vessel; and
means for simultaneously severing the vessel and the extended portion of the flexible suture.

* * * * *